United States Patent
Chen et al.

(10) Patent No.: US 10,792,423 B2
(45) Date of Patent: Oct. 6, 2020

(54) METHODS, SYSTEMS, AND COMPUTER READABLE MEDIA FOR PHYSIOLOGY PARAMETER-INVARIANT MEAL DETECTION

(71) Applicant: The Trustees of the University of Pennsylvania, Philadelphia, PA (US)

(72) Inventors: Sanjian Chen, Philadelphia, PA (US); James Erich Weimer, Philadelphia, PA (US); Insup Lee, Newtown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 369 days.

(21) Appl. No.: 15/487,179

(22) Filed: Apr. 13, 2017

(65) Prior Publication Data
US 2017/0296746 A1    Oct. 19, 2017

Related U.S. Application Data

(60) Provisional application No. 62/322,003, filed on Apr. 13, 2016.

(51) Int. Cl.
| | |
|---|---|
| *A61M 5/172* | (2006.01) |
| *A61B 5/145* | (2006.01) |
| *A61B 5/00* | (2006.01) |
| *G16H 20/17* | (2018.01) |
| *G16H 50/20* | (2018.01) |
| *A61M 5/142* | (2006.01) |
| *A61F 2/02* | (2006.01) |

(52) U.S. Cl.
CPC ....... *A61M 5/1723* (2013.01); *A61B 5/14532* (2013.01); *A61B 5/7275* (2013.01); *A61B 5/7282* (2013.01); *A61F 2/022* (2013.01); *G16H 20/17* (2018.01); *A61B 5/4839* (2013.01); *A61M 2005/14208* (2013.01); *G01N 2800/042* (2013.01); *G16H 50/20* (2018.01)

(58) Field of Classification Search
CPC ...... A61M 5/1723; A61M 2005/14208; G16H 20/17; A61B 5/14532; A61B 5/7275; A61B 5/7282; A61B 5/4839; G01N 2800/042
USPC ........................................................... 705/2
See application file for complete search history.

(56) References Cited

U.S. PATENT DOCUMENTS

2003/0171900 A1*  9/2003  Desai ................. G06K 9/00496
                                                  702/190

OTHER PUBLICATIONS

By Dassau et al., "Detection of a Meal Using Continuous Glucose Monitoring Implications for an Artificial b-cell", Diabetes Care, vol. 31, No. 1, pp. 295-300 (Feb. 2008) (hereinafter Dassau) (Year: 2008).*

(Continued)

*Primary Examiner* — Elaine Gort
*Assistant Examiner* — Christopher B Wehrly
(74) *Attorney, Agent, or Firm* — Jenkin, Wilson, Taylor & Hunt, P.A.

(57) ABSTRACT

Methods, systems, and computer readable media for physiology parameter-invariant meal detection are disclosed. According to one system, the system includes at least one processor and a meal detection module implemented using the at least one processor. The meal detection module is configured to receive insulin intake information and blood glucose level information for a user, to detect a meal event using a physiology parameter-invariant meal detection algorithm, and after detecting the meal event, to perform at least one control action associated with insulin management.

9 Claims, 7 Drawing Sheets

(56) References Cited

OTHER PUBLICATIONS

"UVa/Padova T1DM Metabolic Simulator," Simulation Services at The Epsilon Group, Access from wayback machine https://web.archive.org/web/20160322190916/http://tegvirginia.com/wp-content/uploads/2013/08/Simulation_Services_T1DM_Simulator.pdf, pp. 1-4 (Mar. 22, 2016).

Weimer et al., "Parameter-Invariant Design of Medical Alarms," Parameter-Invariant Design of Medical Alarms, pp. 1-10 (Oct. 2015).

Roederer et al., "Robust Monitoring of Hypovolemia in Intensive Care Patients Using Photoplethysmogram Signals," IEEE Engineering in Medicine and Biology Conference, EMBC 15, pp. 1-5 (Aug. 2015).

Chen et al., "Towards a Model-Based Meal Detector for Type I Diabetics," Medical Cyber-Physical Systems Workshop, http://repository.upenn.edu/cis_papers/782/, pp. 1-12 (Apr. 13, 2015).

Roederer et al., "Towards Non-Invasive Monitoring of Hypovolemia in Intensive Care Patients," Medical Cyber-Physical Systems Workshop 2015, pp. 1-8 (Apr. 13, 2015).

Turksoy et al., "Meal-Detection in Patients with Type 1 Diabetes: A New Module for the Multivariable Adaptive Artificial Pancreas Control System," J. of Biomedical and Health Informatics, IEEE, pp. 1-9 (Jun. 2015).

"Hypoglycemia (Low Blood Glucose)," American Diabetes Association, http://www.diabetes.org/living-with-diabetes/treatment-and-care/blood-glucose-control/hypoglycemia-low-blood.html, pp. 1-5 (Jul. 1, 2015).

Meece, "The Artificial Pancreas: Where We Are, Where We're Going," AADE in Practice, vol. 3, No. 2, pp. 42-44 (Mar. 2015).

Ivanov et al., "Early Detection of Critical Pulmonary Shunts in Infants," Proceedings of the 6th ACM/IEEE International Conference on Cyber-Physical Systems, ICCPS 15, pp. 1-12 (2015).

Harvey et al., "Design of the Glucose Rate Increase Detector a Meal Detection Module for the Health Monitoring System," Journal of Diabetes Science and Technology, vol. 8, No. 2, pp. 307-320 (2014).

"National Diabetes Statistics Report: Estimates of Diabetes and its Burden in the United States," Centers for Disease Control, pp. 1-12 (2014).

Man et al., "The UVA/PADOVA Type 1 Diabetes Simulator New Features," Journal of Diabetes Science and Technology, vol. 8, No. 1, pp. 26-34 (2014).

Weimer et al., "Distributed Model-Invariant Detection of Unknown Inputs in Networked Systems," Internatonial Conference on High Confidence Networked Systems, pp. 127-134 (Apr. 9-11, 2013).

Weimer et al., "Parameter-Invariant Detection of Unknown Inputs in Networked Systems," Conference on Decision and Control, pp. 1-7 (2013).

Weimer et al., "Active Actuator Fault Detection and Diagnostics in HVAC Systems," Proceedings of the Fourth Workshop on Embedded Sensing Systems for Energy-Efficiency in Buildings, pp. 1-8 (Nov. 6, 2012).

Weimer et al., "Distributed Detection and Isolation of Topology Attacks in Power Networks," International Conference on High Condence Networked Systems, pp. 65-71 (Apr. 17-18, 2012).

Lee et al., "Challenges and Research Directions in Medical Cyber-Physical Systems," Proceedings of the IEEE, vol. 100, No. 1, pp. 75-90 (2012).

Cobelli et al., "Artificial Pancreas: Past, Present, Future," Diabetes, vol. 60, No. 11, pp. 2672-2682 (Nov. 2011).

Convertino et al., "Use of Advanced Machine-Learning Techniques for Non-Invasive Monitoring of Hemorrhage," Journal of Trauma-Injury, Infection, and Critical Care, vol. 71, No. 1, pp. 1-12 (2011).

Saria et al., "Integration of Early Physiological Responses Predicts Later Illness Severity in Preterm Infants," Sci Transl Med., vol. 2, No. 48, pp. 1-19 (Sep. 8, 2010).

Pantelopoulos et al., "A Survey on Wearable Sensor-Based Systems for Health Monitoring and Prognosis," IEEE Transactions on Systems, Man, and Cybernetics, Part C: Applications and Reviews, vol. 40, No. 1, pp. 1-12 (Jan. 2010).

Saria et al., "Learning Individual and Population Level Traits from Clinical Temporal Data," Proceedings of Neural Information Processing Systems, pp. 1-9 (2010).

Burgos et al., "Real-Time Detection of Apneas on a PDA," IEEE Transactions on Information Technology in Biomedicine, vol. 14. No. 4, pp. 995-1002 (2010).

Cobry et al., "Timing of Meal Insulin Boluses to Achieve Optimal Postprandial Glycemic Control in Patients with Type 1 Diabetes," Diabetes Technology & Therapeutics, vol. 12, No. 3. pp. 173-177 (2010).

Bruttomesso et al., "Closed-Loop Artificial Pancreas Using Subcutaneous Glucose Sensing and Insulin Delivery and a Model Predictive Control Algorithm: Preliminary Studies in Padova and Montpellier," Journal of Diabetes Science and Technology, vol. 3, Issue 5, pp. 1014-1021 (Sep. 2009).

Cameron et al., "Probabilistic Evolving Meal Detection and Estimation of Meal Total Glucose Appearance," Journal of Diabetes Science and Technology, vol. 3, Issue 5, pp. 1022-1030 (Sep. 2009).

Magni et al., "Model Predictive Control of Glucose Concentration in Type 1 Diabetic Patients: An in Silico Trial," Biomedical Signal Processing and Control. vol. 4, Issue 4, pp. 338-346 (2009).

Lee et al., "A Closed-Loop Artificial Pancreas Using Model Predictive Control and a Sliding Meal Size Estimator," Journal of Diabetes Science and Technology, vol. 3, Issue 5, pp. 1082-1090 (Sep. 2009).

Lee et al., "A Closed-loop Artificial Pancreas Based on Model Predictive Control: Human-Friendly Identification and Automatic Meal Disturbance Rejection," Biomedical Signal Processing and Control, vol. 4 No. 4 pp. 347-354 (2009).

Ellingsen et al., "Safety Constraints in an Artificial Pancreatic β Cell: an Implementation of Model Predictive Control with Insulin on Board," Biomedical Signal Processing and Control, vol. 3, No. 3, pp. 536-544 (2009).

Cobelli et al., "Diabetes: Models, Signals, and Control," Biomedical Engineering, IEEE Reviews, pp. 1-97 (Jan. 1, 2009).

Kovatchev et al., "In Silico Preclinical Trials: A Proof of Concept in Closed-Loop Control of Type 1 Diabetes.," Journal of Diabetes Science and Technology, vol. 3, Issue 1, pp. 44-55 (Jan. 2009).

Gillis et al., "Glucose Estimation and Prediction Through Meal Responses Using Ambulatory Subject Data for Advisory Mode Model Predictive Control," Journal of Diabetes Science and Technology, vol. 1, Issue 6, pp. 825-833 (Nov. 2007).

Magni et al., "Model Predictive Control of Type 1 Diabetes: an in Silico Trial," Journal of Diabetes Science and Technology, vol. 1, Issue 6, pp. 804-812 (Nov. 2007).

Man et al., "Meal Simulation Model of the Glucose-Insulin System," IEEE Transactions on Biomedical Engineering, vol. 54, No. 10, pp. 1740-1749 (Oct. 2007).

Dassau et al., "Detection of a Meal Using Continuous Glucose Monitoring Implications for an Artificial β-cell," Diabetes Care, vol. 31, No. 2, pp. 295-300 (Feb. 2008).

Wilson et al., "The Accuracy of the FreeStyle Navigator Continuous Glucose Monitoring System in Children With Type 1 Diabetes," Diabetes Care vol. 30. No. 1, pp. 59-64 (2007).

Adlassing et al., "Temporal Representation and Reasoning in Medicine: Research Directions and Challenges," Artificial Intelligence in Medicine, vol. 38, pp. 101-113 (2006).

Guelfi et al., "The Decline in Blood Glucose Levels is Less With Intermittent High-Intensity Compared With Moderate Exercise in Individuals With Type 1 Diabetes," Diabetes Care, vol. 28, No. 6, pp. 1289-1294 (Jun. 2005).

Grimm, "Exercise in Type 1 Diabetes," Exercise and Sport in Diabetes, Chapter 2, pp. 25-43 (2005).

Mitchell et al., "Classifying Instantaneous Cognitive States from fMRI Data" AMIA Annual Symposium Proceedings, pp. 465-469 (2003).

Capes et al., "Stress Hyperglycemia and Prognosis of Stroke in Nondiabetic and Diabetic Patients a Systematic Overview," Stroke, vol. 32, No. 10, pp. 2426-2432 (Oct. 2001).

Nucci et al., "Models of Subcutaneous Insulin Kinetics. A Critical Review," Computer Methods and Programs in Biomedicine, vol. 62, Issue 3, pp. 249-257 (2000).

(56) References Cited

OTHER PUBLICATIONS

Wolever et al., "Prediction of Glucose and Insulin Responses of Normal Subjects After Consuming Mixed Meals Varying in Energy, Protein, Fat, Carbohydrate and Glycemic Index," Human and Clinical Nutrition, vol. 126, No. 11, pp. 2807-2812 (1996).
Klein, "Hyperglycemia and Microvascular and Macrovascular Disease in Diabetes," Diabetes Care, vol. 18, Issue 2, pp. 258-268 (1995).
Reichard et al., "The Effect of Long-Term Intensified Insulin Treatment on the Development of Microvascular Complications of Diabetes Mellitus," New England Journal of Medicine, vol. 329, No. 5, pp. 304-309 (Jul. 29, 1993).
Horn et al., "Topics in Matrix Analysis," Cambridge University Press, New York, NY, USA, pp. 1-610 (1991).
Kobayashi et al., "The Pharmacokinetics of Insulin After Continuous Subcutaneous Infusion or Bolus Subcutaneous Injection in Diabetic Patients," Diabetes; vol. 32, Issue 4, pp. 331-336 (Apr. 1983).
Bergman et al. "Quantitative Estimation of Insulin Sensitivity." American Journal of Physiology-Endocrinology and Metabolism, 236(6), pp. E667-E677 (Jul. 1979).
Willsky et al., "A Survey of Design Methods for Failure Detection in Dynamic Systems," Automatica, vol. 12, pp. 601-611 (1976).

\* cited by examiner

METHODS, SYSTEMS, AND COMPUTER READABLE MEDIA FOR PHYSIOLOGY PARAMETER-INVARIANT MEAL DETECTION

PRIORITY CLAIM

This application claims the benefit of U.S. Provisional Patent Application Ser. No. 62/322,003, filed Apr. 13, 2016; the disclosure of which is incorporated herein by reference in its entirety.

GOVERNMENT INTEREST

This invention was made with government support under Grant Nos. CNS-1035715 and U.S. Pat. No. 1,231,680 awarded by the National Science Foundation. The government has certain rights in the invention.

TECHNICAL FIELD

The subject matter described herein relates to insulin management. More specifically, the subject matter relates to methods, systems, and computer readable media for physiology parameter-invariant meal detection.

BACKGROUND

Blood glucose management systems are an important class of medical systems that provide vital everyday decision support service to diabetics. An artificial pancreas, which integrates a continuous glucose monitor, a wearable insulin pump, and control algorithms running on embedded computing devices, can significantly improve the quality of life for millions of Type 1 diabetics. A primary problem in the development of an artificial pancreas is the accurate detection and estimation of meal carbohydrates, which cause significant glucose system disturbances. Meal carbohydrate detection is challenging since post-meal glucose responses greatly depend on patient-specific physiology and meal composition.

Accordingly, there exists a need for methods, systems, and computer readable media for physiology parameter-invariant meal detection.

SUMMARY

Methods, systems, and computer readable media for physiology parameter-invariant meal detection are disclosed. According to one system, the system includes at least one processor and a meal detection module implemented using the at least one processor. The meal detection module is configured to receive insulin intake information and blood glucose level information for a user, to detect a meal event using a physiology parameter-invariant meal detection algorithm, and after detecting the meal event, to perform at least one control action associated with insulin management.

A method for physiology parameter-invariant meal detection is also disclosed. The method includes receiving insulin intake information and blood glucose level information for a user. The method also includes detecting a meal event using a physiology parameter-invariant meal detection algorithm. The method further includes after detecting the meal event, performing at least one control action associated with insulin management.

The subject matter described herein can be implemented in software in combination with hardware and/or firmware. For example, the subject matter described herein can be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the term "node" refers to a physical computing platform or device including one or more processors and memory.

As used herein, the terms "function" and "module" refer to software in combination with hardware and/or firmware for implementing features described herein.

BRIEF DESCRIPTION OF THE DRAWINGS

Embodiments of the subject matter described herein will now be explained with reference to the accompanying drawing, wherein like reference numerals represent like parts, of which.

DETAILED DESCRIPTION

Figure 1:
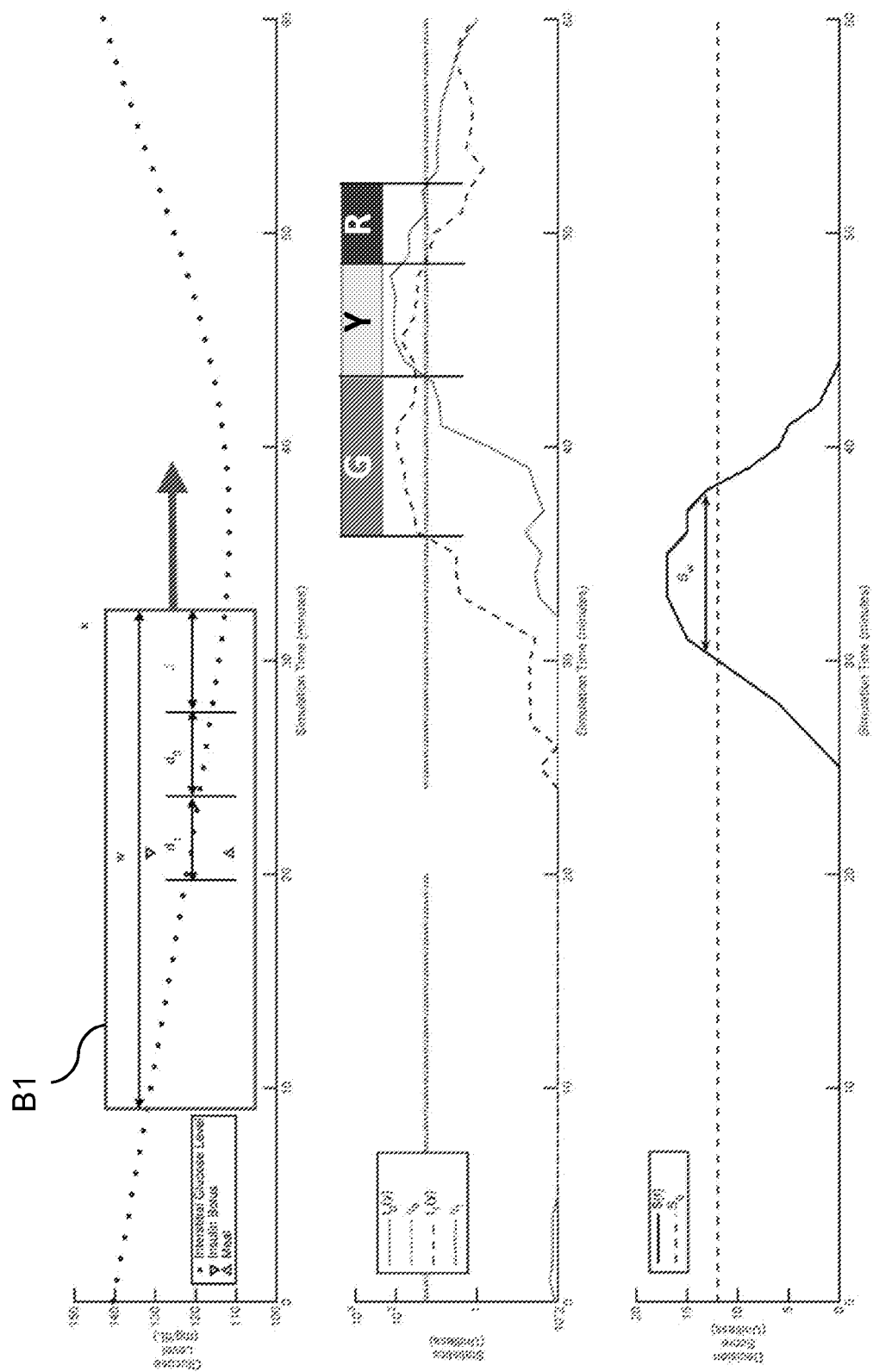
FIG. 1 is a diagram illustrating decision points and related data associated with meal detections.

The subject matter described herein relates to methods, systems, and computer readable media for physiology parameter-invariant meal detection. Type 1 diabetes (T1D) affects approximately 1.25 million people in the United States and 5 million Americans are expected to have T1D by 2050 [11]. T1D patients depend on daily insulin therapy to control glucose levels in order to avoid numerous long-term complications associated with hyperglycemia [19]. Meal carbohydrates cause significant disturbance to one's glucose level and for T1D patients, it is critical to cautiously plan insulin injections around meal times to avoid postprandial hyperglycemia and subsequent post-correction hypoglycemia. Artificial Pancreas (AP) systems [2, 7, 25] aim to regulate the glucose level by automatically delivering insulin and free T1D patients from the cognitive burden of frequent glucose monitoring, carb counting, and insulin dosing decision making.

A significant challenge of meal-time glycemic control is the sensing and action delays: the glucose level starts to rise a certain time after the onset of a meal and there is a delay between the injection of insulin and the action of insulin to dispose of glucose. To cope with this challenge, the AP systems need meal information either by announcement [24] or meal detection [3, 5, 6, 9, 16, 23, 31]. The subject matter described herein relates to accurate and timely meal detection—i.e., detecting if carbohydrates have been ingested in the recent past. Accurate meal detection not only serves as the first step towards meal estimation (i.e., estimating the amount of carbohydrates ingested), but can also be employed by meal estimation algorithms as a safety backup, especially in situations where user input is erroneous [9]. The problems of carbohydrate estimation and insulin bolus calculation [31] are not considered herein and left as future work.

A meal detector aims to identify, in real-time, carbohydrate ingestion based on continuous glucose monitor (CGM) readings. Several meal detection strategies already exist in the literature. Dassau et al. propose a voting-based meal detector that tracks the glucose rate-of-changes (RoCs) estimated by different methods including Kalman Filtering and announces a meal when three out of the four RoC estimates cross pre-specified thresholds [9]. Using similar Kalman Filtering techniques, Lee and Bequette develop a meal detector that announces a meal based on RoCs crossing thresholds and estimates the meal size by feeding the filtered glucose RoCs into a finite response filter [22]. Harvey et al. recently proposed a meal detection algorithm that announces meals based on a two-stage CGM filtering process and RoC criteria [16]. Cameron et al. develop a meal detection algorithm that uses a simple glucose model to match the RoC of the CGM readings to temporal trajectories assuming both no-meal and meal scenarios [3]. All the aforementioned meal detectors require identifying patient-specific parameters (e.g., insulin sensitivity, insulin diffusion rate, etc.), most of which vary with time. Due to the inherent physiological dependency, the RoC based detectors may suffer from high false positives, considering that non-meal disturbance factors may also cause significant glucose fluctuations (e.g. exercising [13], stress [4], and depletion of insulin-on-board [27]). Additionally, the trajectory-matching meal detector has a long average detection delay [15]. As an alternative, recent work by Turksoy et al. simultaneously aims to estimate physiological variables and model parameters to provide accurate meal detection and estimation; however, no guarantees are provided that the physiological parameter estimates converge to their true value [31]. Quick and reliable meal detection is critical for the AP systems: false detections can lead to unnecessary insulin delivery that may trigger life-threatening hypoglycemia; missed detections or significant detection delays can leave the patient with marked postprandial hyperglycemia.

The subject matter described herein includes a novel meal detection algorithm that is based on a commonly accepted minimal glucose physiological model and is "invariant" to individual physiological parameters—i.e., it achieves a near constant false alarm rate (CFAR) across the patient population without needing individual tuning. We compare an example implementation of a parameter invariant (PAIN) meal detector with various aspects described herein with three published meal detection techniques [9, 16, 22]. Evaluations on an FDA-accepted T1D simulator [21] and a real T1D clinical dataset [36] show that our detector outperforms (often significantly) other detectors in multiple aspects: detection rate, false-positive rate, detection delays, and per-subject missed meals.

Methods

In this section, aspects related to meal detection using a parameter invariant (PAIN) design approach [35] usable for achieving a CFAR [30] or near-CFAR is discussed. In many medical monitoring applications, including meal detection, unknown or uncertain patient physiology presents a fundamental challenge in generating mathematical models useful for detector design. The PAIN approach utilizes physiological models and trends to capture the effects of the unknown nuisance parameters, then establishes invariance to the nuisance parameters by projecting the measurements onto a space which is unaffected by the unknown parameters, mathematically known as a null space projection. The benefit of the PAIN approach is that the projected measurements will be the same, regardless of the patient's unknown physiology, allowing the design of powerful detectors that leverage this population-level consistency. PAIN design approaches have been successfully applied to various engineering applications with unknown parameters [32, 33, 34] and have recently been extended to medical monitor design [18, 28, 29, 35].

To present an example PAIN-based meal detector, this section utilizes FIG. 1 as a visual aid and discloses useful mathematics related to its formulation. In some embodiments, meal detection may be performed in two steps. First, at time k in FIG. 1, we use a time window of measurements (denoted by w in FIG. 1) and comparatively test, using PAIN techniques [35], two consecutive sub-windows of time ending $\delta$ time steps before k (represented by $d_0$ and $d_1$ in FIG. 1) for the presence of a meal. The time steps correspond to the CGM sampling period and we use 1-minute sampled CGMs in the in silico study, which is consistent with the sampling rate of the clinical dataset [36]. Second, we sequentially filter the test decisions generated at each time step k to generate a threshold-based test for meal detection. The remainder of this section describes, in detail, various components of the meal detector, namely, modeling glucose-insulin physiological trends, designing physiology-invariant tests, and filtering test decisions.

Modeling Glucose-Insulin Physiological Trends

Many models exist for describing glucose-insulin physiology, ranging from high-fidelity maximal models [8, 21] to an assortment of low-fidelity minimal models [1]. For the PAIN technique to be useful, a chosen model should capture the general physiological trends that discriminate meal occurrence or absence. In some embodiments, to capture the real-life scenario where the glucose level is measured at a subcutaneous site and carbohydrates enter plasma via a digestion pathway, a modified $5^{th}$-order linear Bergman model [1] augmented with minimal compartmental models that describe the subcutaneous insulin pathway [20, 26] and meal carbohydrate digestion pathway [12] is utilized. The complete augmented physiological model is a five-state linear system (discussed further below with reference to Equation 1) and contains several specific physiological parameters, e.g., the insulin sensitivity [1], the insulin diffusion rate [26], and the time of maximum glucose appearance [12]. Identifying these parameters for each individual patient requires time-consuming tests in strictly controlled clinical settings, which may be inaccurate outside the controlled setting. Thus, a core element of our meal detector is the design of tests invariant to the unknown time-varying physiological parameters.

Designing Physiology-Invariant Tests

Applying standard time-series analysis techniques [30], we can write the CGM measurement model at time step k (as shown in FIG. 1), assuming meal window $d_i$ for $i \in \{0,1\}$, as $y_k = H_{k,i}\theta + \sigma n$, where $y_k$ is a vector of the w CGM measurements, and $H_{k,i}$ is a known matrix (defined in Equation 2 discussed below) which relates how the CGM measurements are affected by the lumped-physiological parameters, θ. The value of θ is a function of the unknown physiological variables (the specific mapping of physiological variables to the lumped-parameters is omitted as it is irrelevant in the design of PAIN detectors [30], i.e., designing tests invariant to the lumped-parameters is equivalent to designing invariant to the underlying physiological variables). Additionally, σ represents an unknown uncertainty associated with a zero-mean noise, n. Utilizing the CGM measurement model, we can generate two invariant statistics, $t_0(y_k)$ and $t_1(y_k)$, as defined in Equation 3 discussed below.

In words, for $t_0(y_k)$, CGM measurements are projected onto the null space of $H_{k,0}$ [17], then $t_0(y_k)$ is generated using the ratio of the remaining measurement energy in the space of $H_{k,1}$ to the measurement energy not remaining in $H_{k,1}$. The form of $t_0(y_k)$ is commonly referred to as an F-ratio in the signal processing and statistics literature [30], and has the useful feature that its value is invariant to the noise level σ as well as the lumped-physiological parameters θ. In the context of various aspects of the subject matter described herein, $t_0(y_k)$ represents the ratio of measurement energy aligned with (and only with) the meal effects of $d_1$ to the measurement energy that cannot be explained exclusively by meals within $d_1$. Comparing $t_0(y_k)$ to a threshold $\eta_0$, selected to achieve a specified probability of false alarm, generates a decision. Similarly, $t_1(y_k)$ is generated by first projecting the measurements onto the null space of $H_{k,1}$, then generating an F-statistic using $H_{k,0}$ and comparing to a threshold $\eta_1$.

The selection of PAIN-based meal detector parameters, $d_0$, $d_1$, δ, and w, can significantly affect its performance. In some embodiments, $d_0$, $d_1$, and δ are selected to be 5 time steps and w to be 300 time steps. These values are chosen because they may provide a 'best' detection rates among the range of values evaluated. A discussion of PAIN-based meal detector parameter effects is provided below with a detailed presentation of the test statistics.

Mathematical details and supporting discussion for implementation of parameter invariant detectors (e.g., a PAIN-based meal detector) are discussed herein. Deriving the detector test statistics requires null space transformations, where the null space of an arbitrary matrix X is [17]

$$\langle X \rangle^\perp = \{v | Xv=0\}$$

and has an orthonormal basis transposed, $X^\perp$, satisfying [17]

$$X^\perp \in \{V | \forall v \in \langle X \rangle^\perp, \exists x, V^T x = v \wedge VV^T = I\}$$

where, $V^T$ denotes the transpose of matrix V [17]. The following employs the above notation to present, mathematically, the meal-detector test statistics implemented in various aspects of the subject matter described herein.

For completeness, we begin by stating the augmented $5^{th}$-order linear Bergman model employed in various aspects of the subject matter described herein, $$\begin{bmatrix} \dot{G}(t) \\ \dot{m}(t) \\ \dot{g}(t) \\ \dot{I}(t) \\ \dot{I}_s(t) \end{bmatrix} = \begin{bmatrix} p_1 & 1 & 0 & p_2 & 0 \\ 0 & -t_G^{-1} & t_G^{-1} & 0 & 0 \\ 0 & 0 & -t_G^{-1} & 0 & 0 \\ 0 & 0 & 0 & -k_e & \frac{k_a}{t_G} \\ 0 & 0 & 0 & 0 & -k_a \end{bmatrix} \begin{bmatrix} G(t) \\ m(t) \\ g(t) \\ I(t) \\ I_s(t) \end{bmatrix} + \begin{bmatrix} p_2 \\ 0 \\ D_G(t) \\ 0 \\ u(t) \end{bmatrix} \quad [1]$$

where, G, m, g, I, and $I_s$ denote the physiological state for plasma glucose, plasma glucose appearance rate, digestive compartment glucose, plasma insulin, and subcutaneous insulin, respectively. The insulin bolus and meals are represented by u and $D_G$, respectively. All other variables represent unknown physiological parameters. For a complete discussion of the model in Equation 1 see [5; sec. 4.2]. Applying standard time-series discretization techniques, the model in Equation 1 can be written as a $5^{th}$-order discrete time system, assuming piecewise constant insulin and meal inputs.

Assuming a 1 minute sampling rate, we denote at time step k, the CGM measurement as $x_k$ (as sampled from G), the injected insulin bolus as $u_k$, and write $$y_k = [x_k \ldots x_{k-w}]^T$$

$$F_k = \begin{bmatrix} x_{k-1} & \ldots & x_{k-5} & u_{k-1} & \ldots & u_{k-4} \\ \vdots & \ddots & \vdots & \vdots & \ddots & \vdots \\ x_{k-w-1} & \ldots & x_{k-w-5} & u_{k-w-1} & \ldots & u_{k-w-4} \end{bmatrix}$$

where, we call $y_k$ the measurements (representing a point in the measurement space) and we say $F_k$ spans the measurement space affected by the insulin bolus and physiological dynamics. More importantly, each column of $F_k$ corresponds to the effect, on the measurements, of an unknown lumped-physiological parameter. The mapping of the physiological parameters in Equation 1 to the lumped-physiological parameters is unimportant in implementing a PAIN-based meal detector and consequently omitted from discussion herein.

While $F_k$ spans the measurement space affected by insulin bolus and physiological parameters, it does not (necessarily) span the effect of meals on the measurements. We capture the effect of meals within the hypothesized meal windows, $d_0$ and $d_1$ in FIG. 1, respectively, as $$G_0 = \begin{bmatrix} 0_{(\delta-4)\times(d_0+4)} \\ I_{(d_0+4)} \\ 0_{(w-\delta-d_0)\times(d_0+4)} \end{bmatrix} \text{ and } G_1 = \begin{bmatrix} 0_{(\delta+d_0-4)\times(d_1+4)} \\ I_{(d_1+4)} \\ 0_{(w-\delta-d_0-d_1)\times(d_1+4)} \end{bmatrix}$$

where, $0_{(n)\times(m)}$ denotes an n-by-m matrix of all zeros and $I_{(m)}$ corresponds to the m-dimensional identity matrix. We note that $G_i$ has $d_i+4$ columns (as opposed to $d_i$ columns) since the effect of the most recent hypothesized meal (of unknown magnitude) within the $d_i$ window affects measurements up to 4 time steps later. Thus, we say that $G_i$ spans the measurement subspace affected by meals within $d_i$ (according to the Bergman model).

We write $$H_{k,i} = [F_k G_i], i \in \{0,1\} \quad [2]$$

and say that $H_{k,i}$ spans the measurement subspace affected by the combined effect of parameters corresponding to the physiological dynamics, insulin bolus, and the meals within the $d_i$ time window. Assuming a meal occurs exclusively within the time window $d_i$, then $y_k = H_{k,1}\theta + \sigma n$ as described in the text.

To present the test statistics, we introduce intermediate variables $$r_{k,0} = H_{k,0}^\perp y, \ U_{k,0} = H_{k,0}^\perp G_1$$

$$r_{k,1} = H_{k,1}^\perp y, \ U_{k,1} = H_{k,1}^\perp G_0$$

where, $r_{k,0}$ and $U_{k,0}$ denote the projection of the measurements and projected meal effects for $d_1$ onto the nullspace of $H_{k,0}$, respectively (and vice-versa for $r_{k,1}$ and $U_{k,1}$). In words, $r_{k,0}$ and $U_{k,0}$ denote the measurements and the effects of meals within $d_1$ which cannot be explained by physiological parameters, insulin bolus, and meals occurring within $d_0$. Consequently, to quantify whether the projected measurements and projected meal effects are significantly aligned [30], we write test statistics, $t_i(y_k)$ for $i \in \{0,1\}$, as $$t_i(y_k) = \frac{r_{k,i}^T (I - (U_{k,i}^+)^T (U_{k,i}^+)) r_{k,i}}{r_{k,i}^T (U_{k,i}^+)^T (U_{k,i}^+) r_{k,i}} \quad [3]$$

For $t_0(y_k)$, the numerator denotes the magnitude of the projected measurements aligned with (i.e., in the subspace of) the projected meal effects of $d_1$, while the denominator represents the energy of the projected measurements which cannot be explained exclusively by meals within $d_1$. Thus, large/small values of $t_0(y_k)$ implies that a meal within $d_1$ is likely/unlikely. Similarly, large/small values of $t_1(y_k)$ indicates that a meal within $d_0$ is likely/unlikely.

In order for the test statistic in Equation 2 to be non-trivial, necessitates the selection of $d_0$, $d_1$, $\delta$, and w in FIG. 1 such that all dimensions within in $G_0$ and $G_1$ are non-negative. In some embodiments, $d_0$, $d_1$, and $\delta$ may be selected to be 5 time-steps and w to be 300 time steps for an example PAIN-based meal detector. In general, the performance of a PAIN-based meal detector varies with the selected parameters. Qualitatively, increasing w improves the detector performance as long as the Bergman model remains accurate. At the same time, decreasing $d_0$, $d_1$, and $\delta$ improves detection accuracy (and time-to-detection) so long as the statistics are non-trivial. Quantifying the detector performance is a subject of future work.

FIG. 1 illustrates how an example PAIN-based meal detector works on simulated scenarios generated by the FDA-accepted simulator [21]. Please note that for aesthetics the values of $d_0$, $d_1$, and $\delta$, and w in FIG. 1 are not the same as the values used in the evaluation. The CGM measurements correspond to a one-minute sampling rate of the interstitial glucose level shown in FIG. 1. The true meal happens around time 22 minutes (the pink upper triangle in the top plot of FIG. 1). The example PAIN-based meal detector works in a sliding-window fashion: at time k, the detector run tests on the $d_0$ and $d_1$ windows utilizing the past w CGM measurements; the relevant time windows at time k are scoped by the box labeled 'B1' in FIG. 1; the detector generates a decision at each time and the time windows (as highlighted in the box labeled 'B1') shift forward in time with the detector to generate sequential statistics and (whose values are shown in the second and third sub-figures in FIG. 1). In FIG. 1, as the $d_0$ window approaches the true meal event (the detector never knows when a meal actually happens and tests every time step), the statistic $t_1(y_k)$ (represented by a dotted line in the figure's middle graph) starts rising and becomes separated from $t_0(y_k)$ (represented by a dotted line in the figure's middle graph), indicating a meal is more likely to have occurred in $d_0$ than in $d_1$. Then as the detector moves further ahead, the true meal enters the $d_1$ window, and $t_0(y_k)$ increases while $t_1(y_k)$ decreases, indicating that a meal is more likely in $d_1$ than in $d_0$. This sequential rise and fall of the statistics $t_0(y_k)$ and $t_1(y_k)$ is leveraged to design a sequential test.

Filtering Sequential Test Decisions

To leverage the structured sequential rise and fall of the statistics, we design an algorithm that generates a cumulative decision score based on the residual statistics $r_i(y_k) = t_i(y_k) - \eta_i$ for $i \in \{0,1\}$. The residual statistics have the useful property that an increasingly positive $r_0(y_k)$ implies an increasing likelihood that a meal has occurred in the window $d_1$ (and vice versa). Thus, the algorithm generates an S-score, S(j), for each time step j (assuming S(j) is initialized to zero) and accumulates S-scores according to the rules in Table 1, where a larger S-score indicates a higher confidence in the occurrence of a meal.

TABLE 1

Score Accumulation Rules for S(j) at k

| | $r_0(y_k) > 0$ | $r_0(y_k) \leq 0$ |
|---|---|---|
| $r_1(y_k) > 0$ | Meal in $d_0$ or $d_1$ + $r_1(y_k)$ to $j \in d_0$ $r_0(y_k)$ to $j \in d_1$ | Meal in $d_0$ + 2 * $r_1(y_k)$ to $j \in d_0$ |
| $r_1(y_k) \leq 0$ | Meal in $d_1$ + 2 * $r_0(y_k)$ to $j \in d_1$ | No Meal Do not change S(j) |

At every step, when the detector claims a meal occurs in window $d_0$, we add $2*r_1(y_k)$ to S(j) for each time step j in the $d_0$ window; similarly, if the detector claims a meal occurs in $d_1$, we add $2*r_0(y_k)$ to S(j) for each time step in the $d_1$ window. If it is likely that a meal was in both windows, then we add $r_1(y_k)$ to S(j) for each time step in the $d_0$ and similarly, we add $r_0(y_k)$ to S(j) of each time step in the $d_1$. Note that we drop the factor of 2 in the increments when both residual statistics, $r_0(y_k)$ and $r_0(y_k)$, are positive, thus weakening the confidence of a meal happening in any individual window. If both residual statistics are negative, then neither $d_0$ nor $d_1$ is likely to contain a meal; thus, no score accumulation occurs.

The score accumulation rules are shaded in FIG. 1: each shaded region corresponds to the rule in Table 1 that applies in that region. In a typical positive meal detection scenario, one should first see the 'green' region (labeled with a 'G' in FIG. 1 and corresponding to the $d_0$ window) approaches the meal event, followed by the 'yellow' region (labeled with a 'Y' in FIG. 1) as the meal event transitions from $d_0$ to $d_1$, and finally see the 'red' region (labeled with a 'R' in FIG. 1), after which a peak in the S(t) curve emerges, indicating that the detector makes a series of decisions at sequential time steps that all point to the same meal time region where the S(t) peak emerges. The magnitude of S(t) corresponds to our confidence in a meal occurring at time t. To trigger an alarm (indicating a meal has occurred), we utilize two design parameters, a threshold $S_0$ and a minimum width $S_w$; a peak is characterized by at least $S_w$ consecutive S(j)'s that are above $S_0$. At each time step, the detector raises a meal alarm if a new S(t) peak emerges. The parameters $S_0$ and $S_w$ can be tuned to achieve different detection performance: smaller $S_0$ and $S_w$ result in higher sensitivity but more false alarms. We note that there is a few steps delay between the actual meal time and the S(t) peak, as shown in FIG. 1. This delay phenomenon is consistently observed in the in silico studies and is related to the physiological fact that there is a delay from the onset of eating to when the CGM reading starts changing: in the maximal model, meal carbohydrates have to pass several digestion compartments before affecting the plasma glucose.

Results

This section presents the evaluation results of an example implementation of a PAIN-based meal detector with various aspects described herein and three existing meal detection algorithms. We compare the performance of detectors in both an in silico clinical trial and on a real clinical dataset.

In Silico Experimental Results

We compare the tested PAIN-based meal detector with three existing meal detectors: the Dassau et al.'s detector [9], Harvey et al.'s detector [16], and Lee and Bequette's detector [22]. We evaluate the detectors in an in silico clinical trial using the academic version of the FDA-accepted T1DMS simulator [14, 8]. A "virtual subject" in the T1DMS simulator is a realization of the 32 physiological parameters. The academic version of the T1DMS simulator contains 10 adult virtual subjects that are sampled from the same parameter distribution of the FDA-accepted population.

The simulation configuration mimics the daily glucose management scenario of a T1D patient. Each virtual subject is fed three meals a day with randomized carb counts. Patient may check their glucose level every two hours and take correctional boluses if glucose levels are high. The meal-time boluses and correctional boluses are calculated based on personalized meal ratio and insulin sensitivity parameters, which are included in the T1DMS simulator. Those parameters are perturbed by a random variation at each meal time and glucose check-point, in order to simulate real-life variation factors such as time-varying meal and insulin responses.

Figure 2:
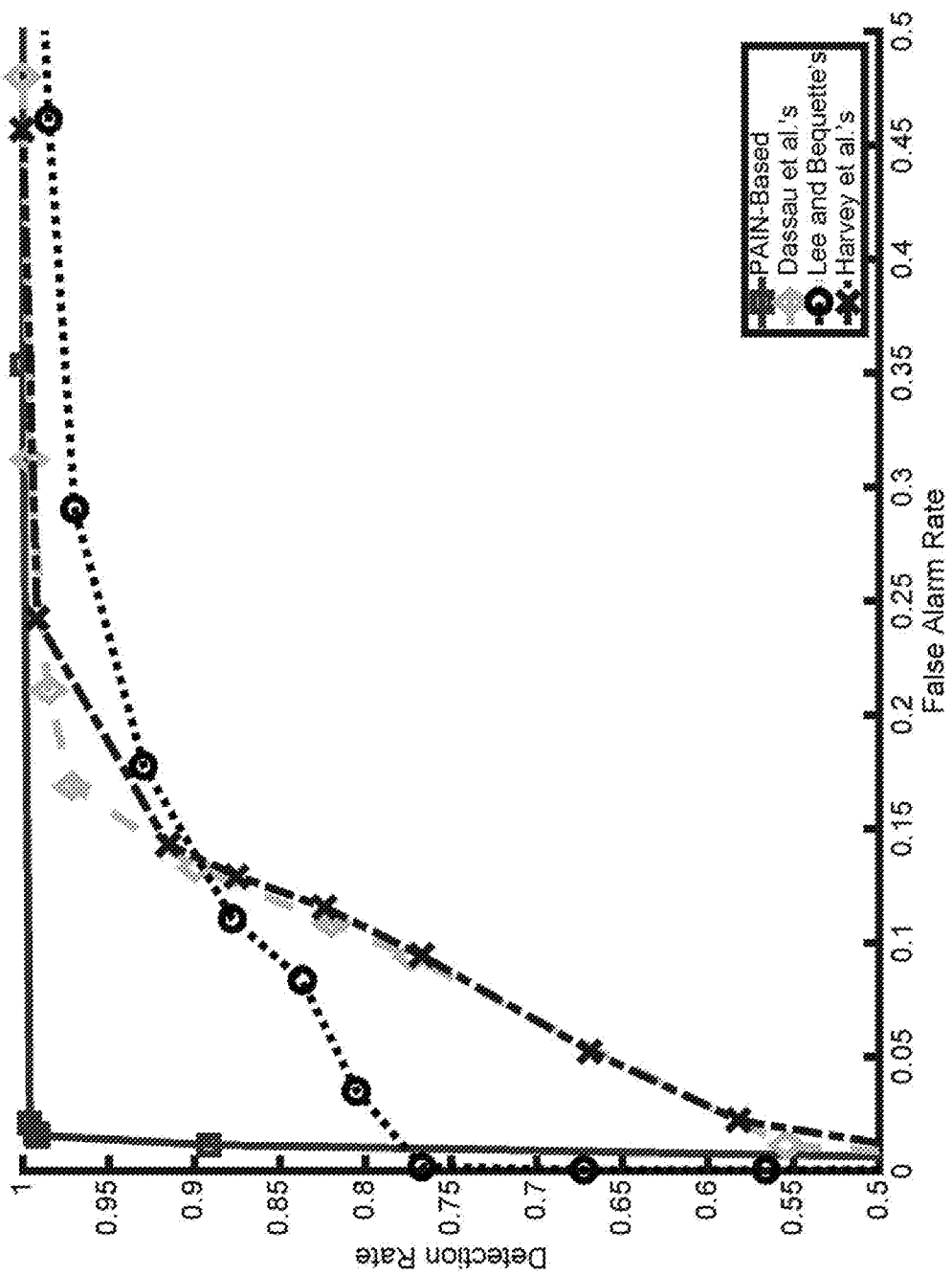
FIG. 2 is a diagram illustrating receiver operating characteristic (ROC) curves of four meal detectors.

We run the tested PAIN-based meal detector, the Dassau et al.'s detector, Harvey et al.'s detector, and Lee and Bequette's detector using the same glucose measurements from the 10 adult virtual subjects in a 300-day in silico trial. Each of the four meal detectors has a set of configurable parameters, e.g., the threshold $S_0$ of the tested PAIN-based meal detector and RoC thresholds of the RoC-based detectors. We systematically explore the combinations of each detector's parameters and get its best detection performance. A receiver operating characteristic (ROC) curve represents the detection rate and false alarm rate of a detector under different configurations. FIG. 2 shows the ROC curves of the four detectors. Table 2 lists a 'best' operating point of each detector. As used herein, a 'best' operating point may be the one that is closest to the theoretical perfect operating point of 100% sensitivity and 0% false alarm rate (100% specificity). The tested PAIN-based meal detector has a number of near-perfect operating points, e.g., the one reported in Table 2 is at the 99.1% sensitivity (meaning that the detector correctly detects 99.1% of meal events within 2 hours) and 1.5% false alarm rate, i.e., on average, the tested PAIN-based meal detector has one missed true meal event every 37 days and one false alarm every 22 days. Here we follow the established convention [16] of using the false alarm rate, instead of the classical notion of specificity, to quantify the meal detection performance. In the sequential time-series meal detection, there is no clear definition of what counts as one "true negative" (no meal presence) discrete event. Therefore the classical specificity definition cannot be applied.

TABLE 2

Operating Points of the Four Detectors

| Detector | Detection Rate | False Alarm Rate |
|---|---|---|
| PAIN-based | 99.1% | 1.5% |
| Dassau et al.'s | 89.9% | 13.3% |
| Lee and Bequette's | 87.8% | 11.0% |
| Harvey et al.'s | 91.6% | 14.3% |

Figure 3:
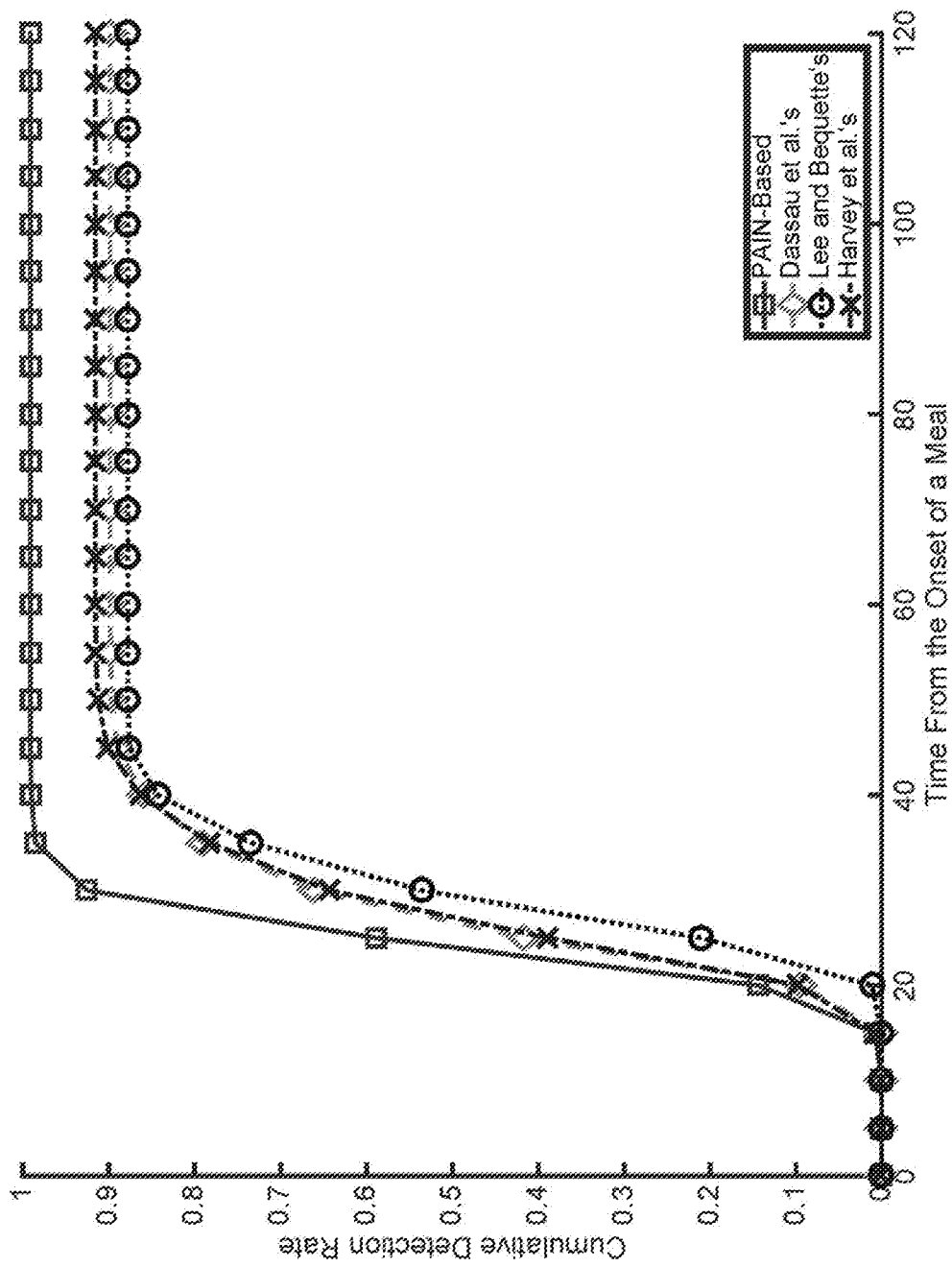
FIG. 3 is a diagram illustrating cumulative detection rates of four meal detectors from the onsets of meals.

FIG. 3 shows the cumulative detection rate from the onsets of meals when running the detectors at their 'best' operating points in the in silico trial. The tested PAIN-based meal detector dominates the others and detects 99.1% meals within 40 minutes (although the common meal detection accounting rule counts any detection within 2 hours of the true meal event as true positives [16]), with a mean detection time of 24 minutes. The other three detectors have longer detection delays and lower maximum detection rates.

Figure 4:
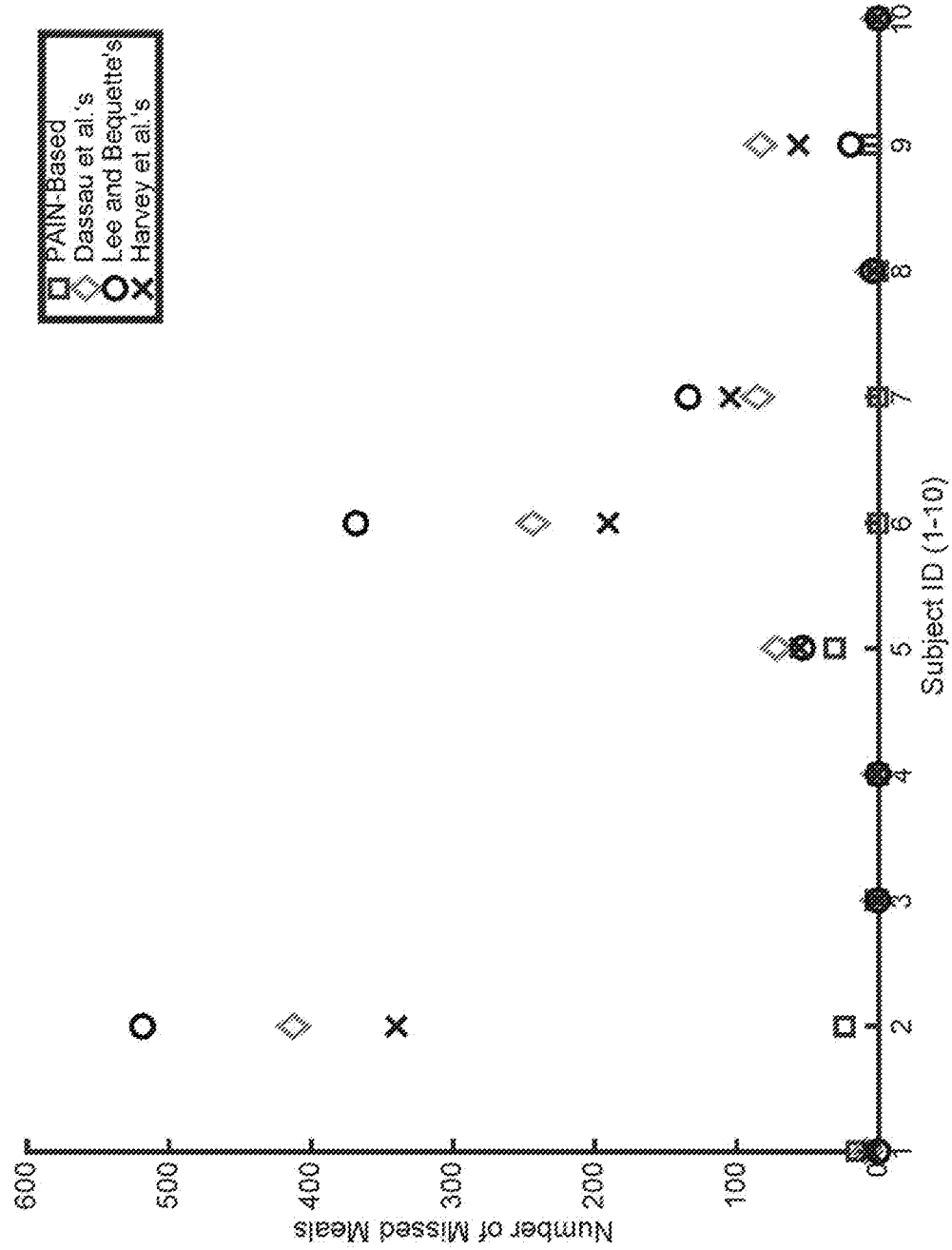
FIG. 4 is a diagram illustrating the per-subject misses of four meal detectors.

FIG. 4 compares the per-subject misses of the four detectors, which is a measure of the consistency of detection performance, i.e., whether a detector can perform particularly bad on any subject. The tested PAIN-based meal detector never misses more than 31 meal events (i.e., 3.5% out of all 900 meals in 300 simulation days) on any of the 10 virtual subjects. In sharp contrast to the tested PAIN-based meal detector, all other three detectors miss a significant portion of the meals on certain subjects, e.g., subject No. 2 and No. 6.

Validation of Detectors on a Clinical Dataset

To further validate the in silico evaluation results, we ran the four detectors on a retrospective clinical dataset collected from a DirecNet pilot study [36]. The clinical dataset includes one-minute CGM readings from 21 T1D patients (age 11±4 years, height 147±23 cm, body weight 45±20 kg, duration of diabetes 5±3 years, HbA1c 7.0%±0.5%). The patients receive a meal challenge test at a clinical research center, during which the insulin bolus is withheld for one hour after the breakfast.

Figure 5:
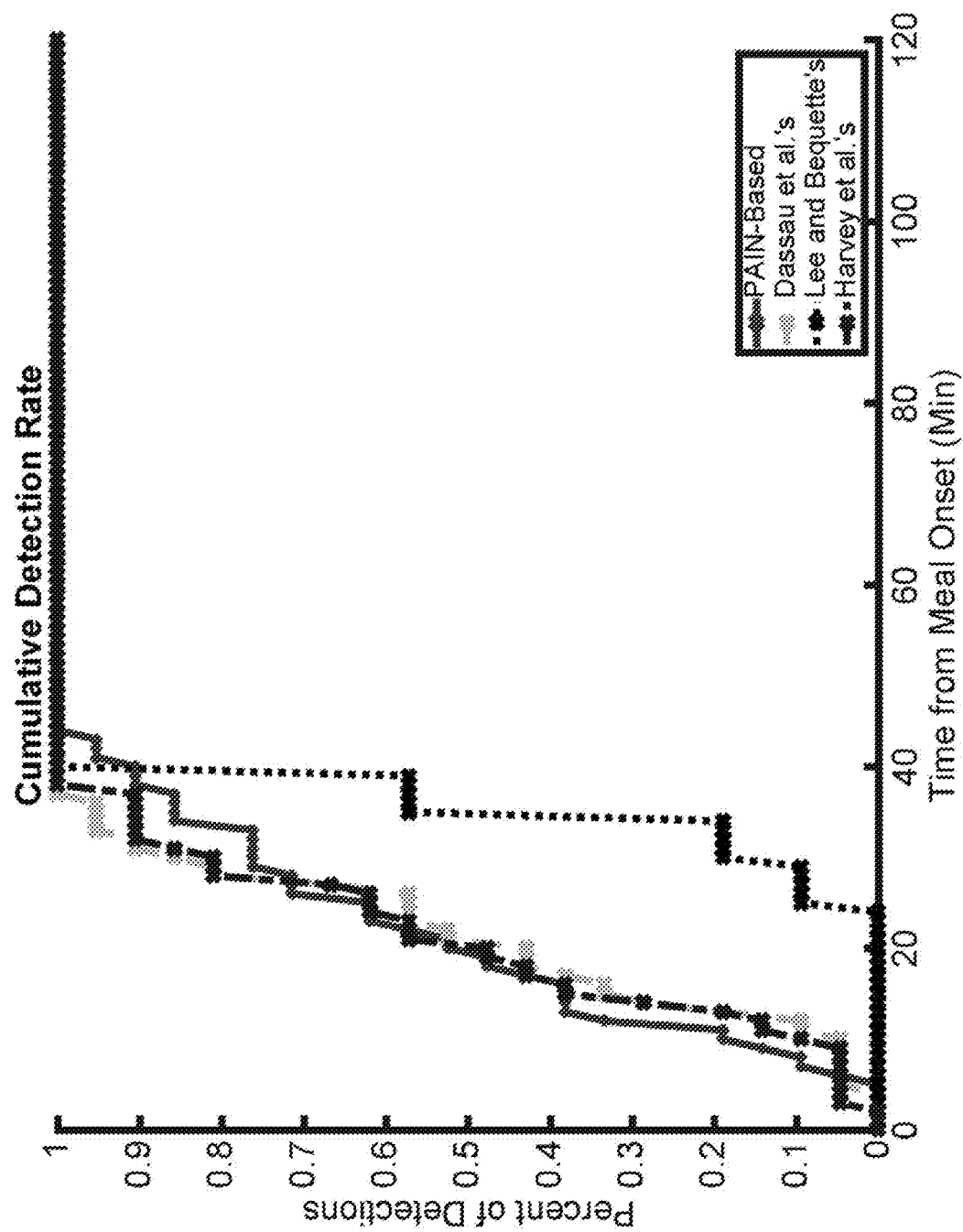
FIG. 5 is a diagram illustrating cumulative detection rate curves of four meal detectors running at operating points identified in the in silico trial.

We evaluate the four detectors on the testing-breakfast of each patient. FIG. 5 shows the cumulative detection rate curves of the four detectors running at their 'best' operating points identified in the in silico trial. The mean detection time of the tested PAIN-based meal detector, Dassau et al.'s detector, and Harvey et al.'s detector is 21 minutes. The mean detection time of Lee and Bequette's detector is 35 minutes. All four detectors are able to detect all meals within two hours.

Discussion

The in silico trial results show that an example implementation of a PAIN-based meal detector with various aspects described herein significantly improves the detection performance when compared with the other three detectors. For example, compared to Harvey et al.'s detector, the tested PAIN-based meal detector reduces the number of false alarms by 90% and reduces the number of missed detections by 88% at the same time in the 10-subjects in-silico study. In terms of detection delay during the in silico trial, the tested PAIN-based meal detector has the shortest mean detection delay and achieves its near-perfect maximum detection rate ahead of all others. The per-subject miss distribution result validates the unique strength of the tested PAIN-based meal detector: it is "invariant" to differences in patients' physiological parameters and thereby achieves highly consistent detection performance across the virtual patient population. This unique feature of the tested PAIN-based meal detector is critical to the safety of artificial pancreas: A meal detector that frequently misses true meal events on some subjects could result in severe post-prandial hyperglycemia and possibly subsequent hypoglycemia "overshoots" of large insulin boluses (to correct the high glucose level). It is worth noting that although we do not implement Cameron et al.'s detector and explicitly compare it with the others in the in silico trial, their original paper also uses the T1DMS for evaluation and reports average detection delay of greater than 50 minutes [3]. In addition, Cameron et al.'s detector requires identifying patient-specific insulin sensitivity profiles. In theory, the performance of the RoC-based detectors may be further improved by carefully tuning the detector parameters for each individual patient. However, such tuning process may require frequent clinic visits because patients' physiological characteristics change over time. Moreover, even with parameter tuning, the RoC-based meal detectors have their fundamental limitation because the post-meal glucose rise rate depends on many other factors such as the nutrition composition of meals [37] and insulin-on-board [10], which can not be mitigated by simply tuning the threshold parameters. In contrast, the in silico trial demonstrates that the tested PAIN-based meal detector is able to achieve consistent performance without any individual-level parameter tuning.

Evaluation result on the DirecNet clinical dataset shows that the tested PAIN-based meal detector detects all meals within about 40 minutes and the mean detection delay is 21 minutes, which is consistent with the in silico trial results. Dassau et al.'s detector and Harvey et al.'s detector also exhibit consistent performance in the in silico trial and retrospective test on the clinical dataset (Dassau et al.'s original paper uses the same DirecNet dataset for evaluation [9]). Compared to the in silico trial results, Lee and Bequette's detector has a slightly longer mean detection delay. This may due to the relatively limited population size of the DirecNet dataset.

Comparing the results over the DirecNet clinical data illustrates that the tested PAIN-based meal detector achieves a similar performance as the detectors of Dassau et al. and Harvey et al. This is due, in large part, to the fact that the DirecNet clinical data was collected in a laboratory setting over the course of one breakfast test while withholding the insulin bolus. Withholding insulin for the meal size in the experiments results in a significant rise in blood glucose which is (often) detectable by RoC detectors. In scenarios where the meal size is reduced and/or an insulin bolus is administered at meal time (possibly via human request) we anticipate the clinical results would be similar to those in the in silico trial. Regardless, the significance of the clinical data results is that the tested PAIN-based meal detector has detection delays consistent with the in silico trial and is not outperformed by the RoC detectors in the literature.

Further Thoughts

The subject matter described herein includes various aspects, methods, systems, and/or techniques related to PAIN-based meal detection, e.g., a PAIN-based meal detector that is based on a physiological model. The in silico trial and evaluation on a clinical dataset demonstrate that an example implementation of a PAIN-based meal detector with various aspects described herein has significantly better detection performance than three existing meal detectors. In addition, the evaluation results validate that the tested PAIN-based meal detector has the unique strength of achieving highly consistent performance across a virtual patient population, with varying physiology, without any individual-level parameter tuning. The high detection rate, low false alarm rate, and consistent inter-subject performance indicate that the tested PAIN-based meal detector and/or other meal detection with various aspects described herein can serve as a reliable meal detection component in artificial pancreases to inform closed-loop controller or be the safety back up for user-provided meal information or other meal detectors.

REFERENCES

[1] Richard N Bergman, Y Ziya Ider, Charles R Bowden, and Claudio Cobelli. Quantitative estimation of insulin sensitivity. American Journal of Physiology-Endocrinology And Metabolism, 236(6):E667, 1979.
[2] Daniela Bruttomesso, Anne Farret, Silvana Costa, Maria Cristina Marescotti, Monica Vettore, Angelo Avogaro, Antonio Tiengo, Chiara Dalla Man, Jerome Place, Andrea Facchinetti, Stefania Guerra, Lalo Magni, Giuseppe De Nicolao, Claudio Cobelli, Eric Renard, and Alberto Maran. Closed-loop artificial pancreas using subcutaneous glucose sensing and insulin delivery and a model predictive control algorithm: preliminary studies in padova and montpellier. Diabetes Sci Technol, 3(5), 2009.
[3] Fraser Cameron, Günter Niemeyer, and Bruce A Buckingham. Probabilistic evolving meal detection and estimation of meal total glucose appearance. Journal of diabetes science and technology, 3(5):1022-1030, 2009.
[4] Sarah E Capes, Dereck Hunt, Klas Malmberg, Parbeen Pathak, and Hertzel C Gerstein. Stress hyperglycemia and prognosis of stroke in nondiabetic and diabetic patients a systematic overview. Stroke, 32(10):2426-2432, 2001.
[5] Sanjian Chen, James Weimer, Michael Rickels, Amy Peleckis, and Insup Lee. Towards a model-based meal detector for type I diabetics. In Medical Cyber-Physical Systems Workshop 2015, 2015. http://repository.upenn.edu/cis_papers/782/
[6] Claudio Cobelli, Chiara Dalla Man, Giovanni Sparacino, Lalo Magni, Giuseppe De Nicolao, and Boris P. Kovatchev. Diabetes: Models, signals, and control. Biomedical Engineering, IEEE Reviews in, 2, 2009.
[7] Claudio Cobelli, Eric Renard, and Boris Kovatchev. Artificial pancreas: past, present, future. Diabetes, 60(11): 2672-2682, 2011.
[8] Chiara Dalla Man, Francesco Micheletto, Dayu Lv, Marc Breton, Boris Kovatchev, and Claudio Cobelli. The uva/padova type 1 diabetes simulator new features. Journal of diabetes science and technology, 8(1):26-34, 2014.
[9] Eyal Dassau, B Wayne Bequette, Bruce A Buckingham, and Francis J Doyle. Detection of a meal using continuous glucose monitoring implications for an artificial β-cell. Diabetes care, 31(2):295-300, 2008.
[10] Christian Ellingsen, Eyal Dassau, Howard Zisser, Benyamin Grosman, Matthew W Percival, Lois Jovanovic, and Francis J Doyle. Safety constraints in an artificial pancreatic β cell: an implementation of model predictive control with insulin on board. Journal of diabetes science and technology, 3(3):536-544, 2009.
[11] Centers for Disease Control, Prevention, et al. National diabetes statistics report: estimates of diabetes and its burden in the united states, 2014. Atlanta, Ga.: US Department of Health and Human Services, 2014.
[12] Rachel Gillis, Cesar C Palerm, Howard Zisser, Lois Jovanovic, Dale E Seborg, and Francis J Doyle. Glucose estimation and prediction through meal responses using ambulatory subject data for advisory mode model predictive control. Journal of diabetes science and technology, 1(6):825-833, 2007.
[13] J Grimm. Exercise in type 1 diabetes. Exercise and sport in diabetes, pages 25-43, 2005.
[14] The Epsilon Group. Uva/padova t1dm metabolic simulator.
[15] Kym J Guelfi, Timothy W Jones, and Paul A Fournier. The decline in blood glucose levels is less with intermittent high-intensity compared with moderate exercise in individuals with type 1 diabetes. Diabetes Care, 28(6): 1289-1294, 2005.
[16] Rebecca A Harvey, Eyal Dassau, Howard Zisser, Dale E Seborg, and Francis J Doyle. Design of the glucose rate increase detector a meal detection module for the health monitoring system. Journal of diabetes science and technology, page 1932296814523881, 2014.

[17] Roger A. Horn and Charles R. Johnson, editors. Matrix Analysis. Cambridge University Press, New York, N.Y., USA, 1986.

[18] Radoslav Ivanov, James Weimer, Allan Simpao, Mohamed Rehman, and Insup Lee. Early detection of critical pulmonary shunts in infants. In Proceedings of the 6th ACM/IEEE International Conference on Cyber-Physical Systems, ICCPS '15, 2015.

[19] Ronald Klein. Hyperglycemia and microvascular and macrovascular disease in diabetes. Diabetes care, 18(2): 258-268, 1995.

[20] Tetsuro Kobayashi, Shinji Sawano, Tokuji Itoh, Kinori Kosaka, Hiroki Hirayama, and Yasuji Kasuya. The pharmacokinetics of insulin after continuous subcutaneous infusion or bolus subcutaneous injection in diabetic patients. Diabetes, 32(4):331-336, 1983.

[21] Boris P. Kovatchev, Marc Breton, Chiara Dalla Man, and Claudio Cobelli. In silico preclinical trials: A proof of concept in closed-loop control of type 1 diabetes. Diabetes Sci Technol, 3(1):44-55, 2009.

[22] Hyunjin Lee and B Wayne Bequette. A closed-loop artificial pancreas based on model predictive control: Human-friendly identification and automatic meal disturbance rejection. Biomedical Signal Processing and Control, 4(4):347-354, 2009.

[23] Hyunjin Lee, Bruce A Buckingham, Darrell M Wilson, and B Wayne Bequette. A closed-loop artificial pancreas using model predictive control and a sliding meal size estimator. Journal of diabetes science and technology, 3(5):1082-1090, 2009.

[24] Lalo Magni, Davide M. Raimondo, Luca Bossi, Chiara Dalla Man, Giuseppe De Nicolao, Boris Kovatchev, and Claudio Cobelli. Model predictive control of type 1 diabetes: an in silico trial. Diabetes Sci Technol, 1(6): 804-812, 2007.

[25] Jerry Meece. The artificial pancreas where we are, where we're going. AADE in Practice, 3(2):42-44, 2015.

[26] Gianluca Nucci and Claudio Cobelli. Models of subcutaneous insulin kinetics. a critical review. Computer methods and programs in biomedicine, 62(3):249-257, 2000.

[27] Per Reichard, Bengt-Yngve Nilsson, and Urban Rosenqvist. The effect of long-term intensified insulin treatment on the development of microvascular complications of diabetes mellitus. New England Journal of Medicine, 329(5):304-309, 1993.

[28] Alexander Roederer, James Weimer, Joseph Dimartino, Jacob Gutsche, and Insup Lee. Towards non-invasive monitoring of hypovolemia in intensive care patients. In Medical Cyber-Physical Systems Workshop 2015, 2015.

[29] Alexander Roederer, James Weimer, Joseph Dimartino, Jacob Gutsche, and Insup Lee. Robust monitoring of hypovolemia in intensive care patients using photoplethysmogram signals. In IEEE Engineering in Medicine and Biology Conference, EMBC '15, 2015.

[30] Louis L Scharf. Statistical signal processing, volume 98. Addison-Wesley Reading, M A, 1991.

[31] K. Turksoy, S. Samadi, J. Feng, E. Littlejohn, L. Quinn, A. Cinar. Meal-Detection in Patients with Type 1 Diabetes: A New Module for The Multivariable Adaptive Artificial Pancreas Control System. In Biomedical and Health Informatics, IEEE Journal of, PP(99):1-8, 2015.

[32] J. Weimer, S. A. Ahmadi, J. Araujo, et al. Active actuator fault detection and diagnostics in hvac systems. In Proceedings of the Fourth Workshop on Embedded Sensing Systems for Energy-Efficiency in Buildings, pages 107-114, 2012.

[33] J. Weimer, D. Varagnolo, and K. H. Johansson. Distributed model-invariant detection of unknown inputs in networked systems. In International Conference on High Confidence Networked Systems, pages 127-134, 2013.

[34] J. Weimer, D. Varagnolo, M. S. Stankovic, and K. H. Johansson. Parameter-invariant detection of unknown inputs in networked systems. In Conference on Decision and Control, pages 4379-4384, 2013.

[35] James Weimer, Radoslav Ivanov, Alexander Roederer, Sanjian Chen, and Insup Lee. Parameter invariant design of medical alarms. IEEE Design & Test, 32(1):9-16, 2015.

[36] Darrell M Wilson, Roy W Beck, William V Tamborlane, Mariya J Dontchev, Craig Kollman, Peter Chase, Larry A Fox, Katrina J Ruedy, Eva Tsalikian, Stuart A Weinzimer, et al. The accuracy of the freestyle navigator continuous glucose monitoring system in children with type 1 diabetes. Diabetes Care, 30(1):59-64, 2007.

[37] T M Wolever and Claudia Bolognesi. Prediction of glucose and insulin responses of normal subjects after consuming mixed meals varying in energy, protein, fat, carbohydrate and glycemic index. The Journal of nutrition, 126(11):2807-2812, 1996.

The disclosures of the above-mentioned references [1]-[37] are incorporated herein by reference in their entireties.

The foregoing description is for the purpose of illustration only, and not for the purpose of limitation, as the subject matter described herein is defined by the claims.

Some aspects of the present subject matter described herein may include, support, or provide mechanisms, techniques, methods, and/or systems associated with a novel meal detector based on a minimal glucose/insulin metabolism model. In some embodiments, the meal detector may be invariant to patient-specific physiological parameters in the minimal model and may achieve a near constant false alarm rate (CFAR).

Reference will now be made in detail to exemplary embodiments of the subject matter described herein, examples of which are illustrated in the accompanying drawing. Wherever possible, the same reference numbers will be used throughout the drawings to refer to the same or like parts.

Figure 6:
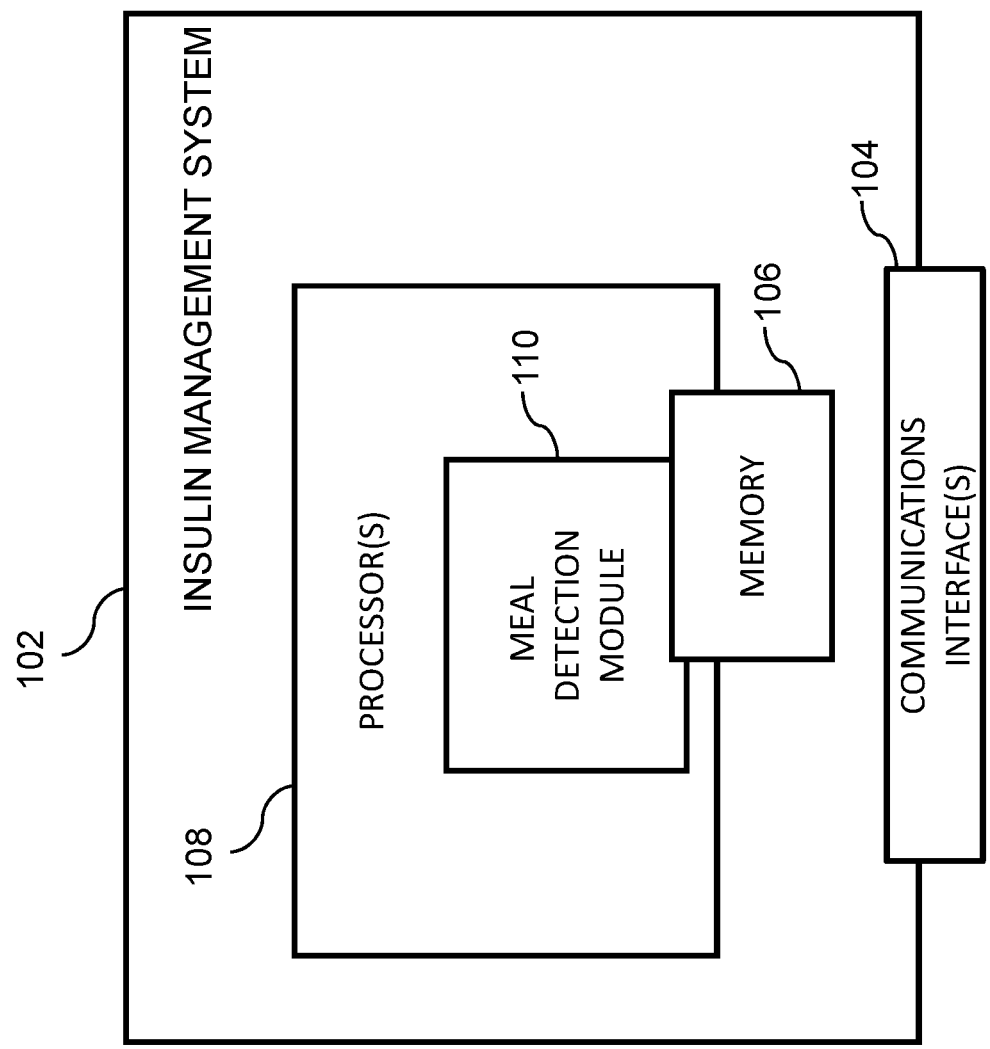
FIG. 6 is a diagram illustrating a system for performing meal detection.

FIG. 6 is a diagram illustrating an example insulin management system 102 (e.g., an embedded chip or system, a processor executing software in an artificial pancreas (AP) system, or an insulin pump) for performing meal detection. Insulin management system 102 may be any suitable entity, such as a computing device, node, or platform, for performing one or more aspects of the present subject matter described herein. In some embodiments, components, modules, and/or portions of insulin management system 102 may be implemented or distributed across multiple devices or computing platforms.

Insulin management system 102 may include various components and/or control modules, e.g., one or more communications interface(s) 104, a memory 106, one or more processors 108, and a meal detection module 110. Communications interface(s) 104 may be any suitable entity or entities (e.g., a communications card or controller) for receiving and/or sending communications. For example, communications interface(s) 104 may allow a meal detection module 110 to interact with various devices and/or components (e.g., a continuous glucose monitor (CGM), an insulin pump, and/or a related component or device of an AP system). In another example, communications interface(s) 104 may be associated with a user interface or other entity (e.g., a configuration tool or device) and may be usable for receiving configuration settings and/or other information associated with insulin management or meal detection.

In some embodiments, communications interface(s) 104 or another component may be configured to interact with a CGM or another device for receiving insulin intake data and/or blood glucose level readings for a user (e.g., a person with Type 1 Diabetes). For example, a CGM may be configured to provide readings and/or other information to insulin management system 102 via communications interface(s) 104 after every reading (e.g., every 5 minutes), periodically, and/or on-demand.

In some embodiments, communications interface(s) 104 or another component may be configured to interact with an insulin pump or other device for triggering one or more insulin management related actions. For example, insulin management system 102 may send, via communications interface(s) 104, commands, messages, other communications to an insulin pump for triggering the insulin pump to release insulin into a user's body or for triggering the insulin pump to stop or cancel a scheduled insulin release. In another example, insulin management system 102 may send, via communications interface(s) 104, commands, messages, or communications to an alarm or other component for notifying a user about a detected meal event.

Memory 106 may be any suitable entity (e.g., random access memory or flash memory) for storing software, logic, and/or information associated with meal detection and/or insulin management. For example, memory 106 112 may store software and/or logic associated with one or more algorithms associated with various aspects or functionality described herein.

In some embodiments, components, such as communications interface(s) 104, meal detection module 110 and software executing on processor(s) 108, of insulin management system 102 may utilize (e.g., read from and/or write to) memory 106. For example, memory 106 may be usable to store historical blood glucose level readings and/or insulin intake data. In another example, memory 106 may be usable to store various scores, detection statistics, test decisions, and/or other information related to meal detection module 110.

Processor(s) 108 represents any suitable entity or entities (e.g., a physical processor, a field-programmable gateway array (FPGA), and/or an application-specific integrated circuit (ASIC)) for performing one or more functions associated with meal detection. Processor(s) 108 may be associated with meal detection module 110. For example, meal detection module 110, e.g., software or algorithms therein, may be implemented using (e.g., executed by) processor(s) 108.

Meal detection module 110 may be any suitable entity or entities (e.g., software executing on at least one processor) for meal detection. In some embodiments, meal detection module 110 may be configured to use one or more techniques, methods, and/or algorithms for detecting a meal event. For example, meal detection module 110 may utilize a physiology parameter-invariant meal detection algorithm. In this example, the physiology parameter-invariant meal detection algorithm may detect a meal event (e.g., when a user ingested a certain number of carbohydrates) based on a minimal glucose/insulin metabolism model and using historical blood glucose level readings (e.g., from a CGM) and historical insulin intake information.

It will be appreciated that FIG. 6 is for illustrative purposes and that various nodes, their locations, and/or their functions may be changed, altered, added, or removed. For example, some nodes and/or functions may be combined into a single entity. In a second example, a node and/or function may be located at or implemented by two or more nodes. Further, it will appreciated that insulin management system 102 may include various components, control modules (e.g., insulin dose titration, glucose prediction, etc.), and/or functions not shown in FIG. 6 or described herein.

Figure 7:
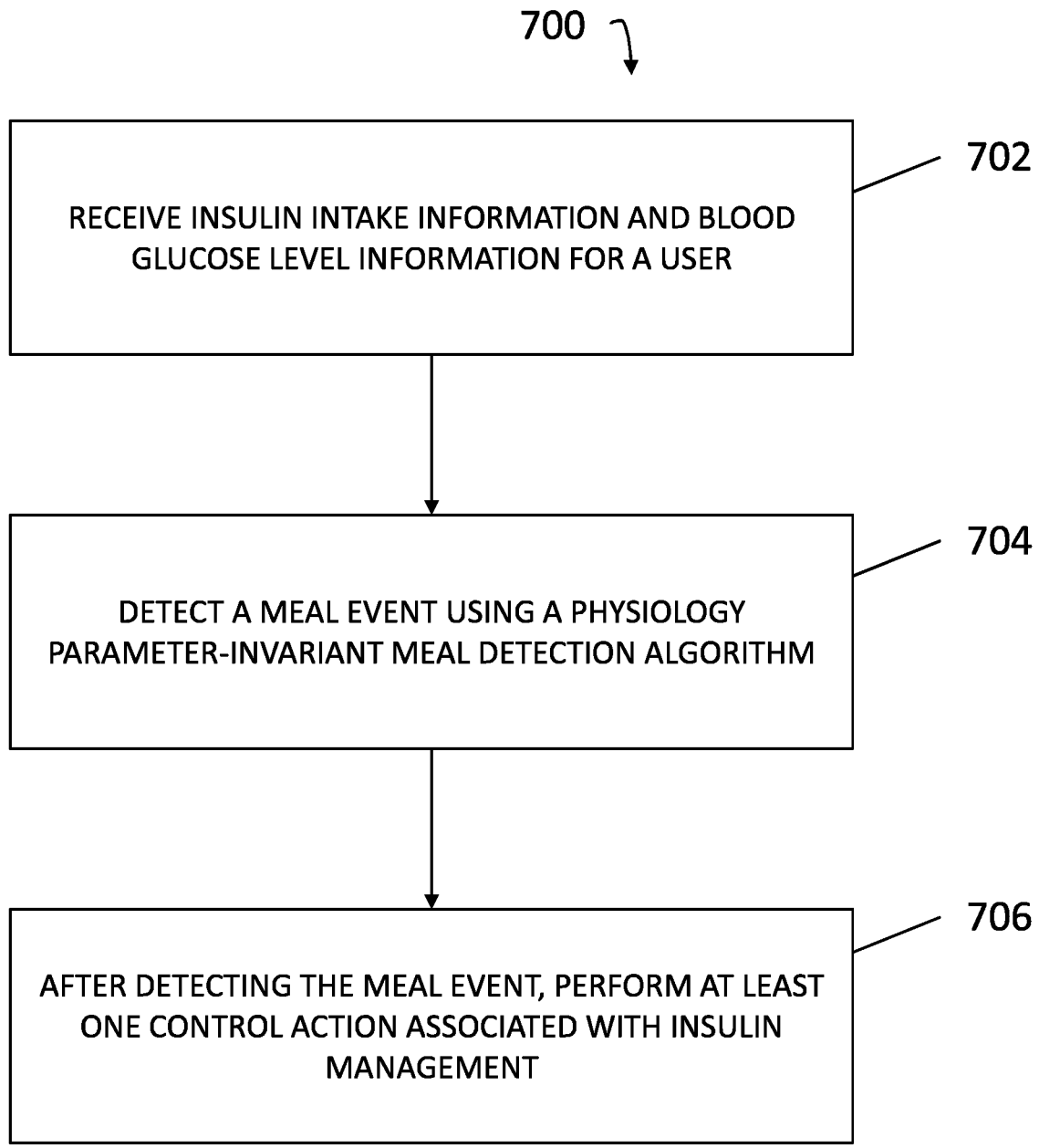
FIG. 7 is a diagram illustrating an example process for performing meal detection.

FIG. 7 is a diagram illustrating an example process 700 for meal detection. In some embodiments, example process 700 may include an algorithm or related logic for physiology parameter-invariant meal detection. In some embodiments, exemplary process 700, or portions thereof, may be performed by or at insulin management system 102, meal detection module 110, a CGM, an AP system, and/or another node or module.

Referring to FIG. 7, in step 702, insulin intake information and blood glucose level information may be received for a user.

In some embodiments, insulin intake information and blood glucose level information may be provided by a user, a CGM, an insulin pump, an AP system, or insulin control system 102.

In step 704, a meal event may be detected, using a physiology parameter-invariant meal detection algorithm.

In some embodiments, a physiology parameter-invariant meal detection algorithm may use a null space projection to detect a meal event regardless of a user's physiology.

In some embodiments, a physiology parameter-invariant meal detection algorithm may use a sliding window of time corresponding to a number of historical blood glucose level readings and historical insulin intake events.

In some embodiments, a physiology parameter-invariant meal detection algorithm may analyze consecutive sub-windows of a sliding window of time associated with historical blood glucose level readings and historical insulin intake events to identify sequential test decisions, e.g., a test decision may indicate that for a given sub-window a meal event is likely or unlikely. In such embodiments, each of the sub-windows may correspond to one or more sampling periods (e.g., blood glucose level readings every five minutes) associated with a CGM.

In some embodiments, a physiology parameter-invariant meal detection algorithm may filter sequential test decisions by generating a cumulative decision score indicative of the likelihood that a meal event occurred.

In some embodiments, a physiology parameter-invariant meal detection algorithm may determine that a meal event occurred when a cumulative decision score exceeds a threshold value for a predetermined amount of time.

In step 706, at least one control action associated with insulin management may be performed after detecting the meal event.

In some embodiments, a control action (e.g., meal detection decisions initiated, triggered or performed by meal detection module 110 or insulin management system 102) may include generating meal event detection decisions, meal event detection scores, meal event alarms, or other output indicating a meal event has occurred. In some embodiments, various outputs from meal detection module 110 may facilitate or include triggering a release of insulin, preventing the release of insulin, and/or triggering a notification or alarm. For example, a control action may include a meal detection decision that is used by an insulin pump or other entity to trigger a release of insulin or adjust an insulin release schedule. In another example, where meal detection module 110 is implemented as a backup meal detection system in a user-inputted meal detection system, meal detection module 110 may notify the user about a detected meal event (e.g., when a meal is detected but no meal was user inputted) such that the user can confirm or deny the detected meal event.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for physiology parameter-invariant meal detection, the method comprising:
    receiving insulin intake information and glucose level information for a user, wherein the glucose level information is obtained from a number of historical glucose level readings taken before or after one or more meal events involving the user and the insulin intake information is obtained from a number of historical insulin intake events including one or more insulin bolus events occurring at or during the one or more meal events;
    detecting a meal event using a physiology parameter-invariant meal detection algorithm, wherein the physiology parameter-invariant meal detection algorithm uses a null space projection to detect the meal event regardless of the user's insulin sensitivity and insulin diffusion rate, wherein the physiology parameter-invariant meal detection algorithm uses a sliding window of time corresponding to the historical glucose level readings and historical insulin intake events, wherein the physiological parameter-invariant meal detection algorithm includes generating an F-statistic for indicating a ratio of measurement energy aligned with meal effects in a sub-window of the sliding window of time to other measurement energy in the sub-window, wherein the F-statistic indicates a test decision for the sub-window, wherein the physiology parameter-invariant meal detection algorithm analyzes consecutive sub-windows of the sliding window to identify sequential test decisions, wherein the physiology parameter-invariant meal detection algorithm filters the sequential test decisions by generating a cumulative decision score indicative of the likelihood that the meal event occurred, wherein the physiology parameter-invariant meal detection algorithm determines that the meal event occurred when the cumulative decision score exceeds a threshold value for a predetermined amount of time; and
    after detecting the meal event, performing at least one control action associated with insulin management, wherein the at least one control action includes triggering a release of insulin or preventing the release of insulin by an insulin pump.

2. The method of claim 1 wherein the insulin intake information and the glucose level information is provided by the user, a continuous glucose monitor (CGM), the insulin pump, an artificial pancreas (AP) system, or an insulin control system.

3. The method of claim 1 wherein the at least one control action includes generating a meal detection decision, generating a meal detection score, generating a meal detection alarm, generating an alarm indicating the meal event has occurred, or triggering a notification or alarm.

4. The method of claim 1 wherein each of the sub-windows corresponds to one or more sampling periods associated with a continuous glucose monitor (CGM).

5. A system for physiology parameter-invariant meal detection, the system comprising:
    at least one processor; and
    a meal detection device implemented using the at least one processor, the meal detection device configured to receive insulin intake information and glucose level information for a user, wherein the glucose level information is obtained from a number of historical glucose level readings taken before or after one or more meal events involving the user and the insulin intake information is obtained from a number of historical insulin intake events including one or more insulin bolus events occurring at or during the one or more meal events, to detect a meal event using a physiology parameter-invariant meal detection algorithm, wherein the physiology parameter-invariant meal detection algorithm uses a null space projection to detect the meal event regardless of the user's insulin sensitivity and insulin diffusion rate, wherein the physiology parameter-invariant meal detection algorithm uses a sliding window of time corresponding to the historical glucose level readings and historical insulin intake events, wherein the physiological parameter-invariant meal detection algorithm includes generating an F-statistic for indicating a ratio of measurement energy aligned with meal effects in a sub-window of the sliding window of time to other measurement energy in the sub-window, wherein the F-statistic indicates a test decision for the sub-window, wherein the physiology parameter-invariant meal detection algorithm analyzes consecutive sub-windows of the sliding window to identify sequential test decisions, wherein the physiology parameter-invariant meal detection algorithm filters the sequential test decisions by generating a cumulative decision score indicative of the likelihood that the meal event occurred, wherein the physiology parameter-invariant meal detection algorithm determines that the meal event occurred when the cumulative decision score exceeds a threshold value for a predetermined amount of time, and after detecting the meal event, to perform at least one control action associated with insulin management, wherein the at least one control action includes triggering a release of insulin or preventing the release of insulin by an insulin pump.

6. The system of claim 5 wherein the insulin intake information and the glucose level information is provided by the user, a CGM, the insulin pump, an artificial pancreas (AP) system, or an insulin control system.

7. The system of claim 5 wherein the at least one control action includes generating a meal detection decision, generating a meal detection score, generating a meal detection alarm, generating an alarm indicating the meal event has occurred, or triggering a notification or alarm.

8. The system of claim 5 wherein the physiology parameter-invariant meal detection algorithm analyzes consecutive sub-windows of the sliding window to identify sequential test decisions, wherein each of the sub-windows corresponds to one or more sampling periods associated with a continuous glucose monitor (CGM).

9. A non-transitory computer readable medium having stored thereon executable instructions that when executed by at least one processor of a computer cause the computer to perform steps comprising:
    receiving insulin intake information and glucose level information for a user, wherein the glucose level information is obtained from a number of historical glucose level readings taken before or after one or more meal events involving the user and the insulin intake information is obtained from a number of historical insulin intake events including one or more insulin bolus events occurring at or during the one or more meal events;

detecting, using a physiology parameter-invariant meal detection algorithm, a meal event, wherein the physiology parameter-invariant meal detection algorithm uses a null space projection to detect the meal event regardless of the user's insulin sensitivity and insulin diffusion rate, wherein the physiology parameter-invariant meal detection algorithm uses a sliding window of time corresponding to the historical glucose level readings and historical insulin intake events, wherein the physiological parameter-invariant meal detection algorithm includes generating an F-statistic for indicating a ratio of measurement energy aligned with meal effects in a sub-window of the sliding window of time to other measurement energy in the sub-window, wherein the F-statistic indicates a test decision for the sub-window, wherein the physiology parameter-invariant meal detection algorithm analyzes consecutive sub-windows of the sliding window to identify sequential test decisions, wherein the physiology parameter-invariant meal detection algorithm filters the sequential test decisions by generating a cumulative decision score indicative of the likelihood that the meal event occurred, wherein the physiology parameter-invariant meal detection algorithm determines that the meal event occurred when the cumulative decision score exceeds a threshold value for a predetermined amount of time; and after detecting the meal event, performing at least one control action associated with insulin management, wherein the at least one control action includes triggering a release of insulin or preventing the release of insulin by an insulin pump.

* * * * *